US008679241B2

(12) United States Patent
Turner et al.

(10) Patent No.: US 8,679,241 B2
(45) Date of Patent: Mar. 25, 2014

(54) GAS PRESSURE MONITOR FOR PNEUMATIC SURGICAL MACHINE

(75) Inventors: Denis Turner, Vista, CA (US); Robert Palino, Aliso Viejo, CA (US)

(73) Assignee: Novartis AG, Basel (CH)

( * ) Notice: Subject to any disclaimer, the term of this patent is extended or adjusted under 35 U.S.C. 154(b) by 1523 days.

(21) Appl. No.: 11/554,387

(22) Filed: Oct. 30, 2006

(65) Prior Publication Data
US 2008/0168985 A1   Jul. 17, 2008

(51) Int. Cl.
*B01D 49/00* (2006.01)

(52) U.S. Cl.
USPC .............. 96/421; 96/417; 96/418; 55/309

(58) Field of Classification Search
USPC ........ 96/417, 418, 421; 128/200.24; 137/870, 137/883, 599.14, 457, 486; 210/91, 340, 210/85, 341
See application file for complete search history.

(56) References Cited

U.S. PATENT DOCUMENTS

| | | | |
|---|---|---|---|
| 812,162 A | 2/1906 | Bemis | |
| 2,016,746 A | 10/1935 | Ireland | |
| 2,707,389 A | 5/1955 | Fortier | |
| 3,084,674 A | 4/1963 | Watson | |
| 3,646,727 A * | 3/1972 | Wachsmuth | 95/22 |
| 3,703,139 A | 11/1972 | Furlong | |
| 3,726,307 A | 4/1973 | Carman et al. | |
| 3,867,934 A | 2/1975 | Ollivier | |
| 4,075,928 A | 2/1978 | Bitonti | |
| 4,077,567 A | 3/1978 | Ginn et al. | |
| 4,086,804 A | 5/1978 | Ruby | |
| 4,253,480 A * | 3/1981 | Kessel et al. | 137/102 |
| 4,323,064 A | 4/1982 | Hoenig et al. | |
| 4,331,130 A | 5/1982 | Lewicky | |
| 4,344,144 A | 8/1982 | Damico et al. | |
| 4,449,550 A | 5/1984 | Ranalli | |
| 4,476,532 A | 10/1984 | Akiyama et al. | |
| 4,590,935 A | 5/1986 | Ranalli | |
| 4,622,503 A | 11/1986 | Sundblom et al. | |
| 4,650,460 A | 3/1987 | Roizenblatt | |

(Continued)

FOREIGN PATENT DOCUMENTS

DE   39 25 405 A1   2/1991
DE   42 32 586 A1   3/1994

(Continued)

OTHER PUBLICATIONS

Non-Final Office Action, U.S. Appl. No. 11/554,387, Sep. 17, 2009, 23 pages.

(Continued)

*Primary Examiner* — Robert Clemente
*Assistant Examiner* — Karla Hawkins
(74) *Attorney, Agent, or Firm* — Darien Reddick

(57) ABSTRACT

A gas pressure monitor system for a pneumatically-powered surgical machine includes a first transducer, a second transducer, and a controller. The first transducer is located upstream from a filter and is configured to read a first pressure of a gas before the gas enters the filter. The second transducer is located downstream from the filter and is configured to read a second pressure of a gas after the gas exits the filter. The controller is configured to compute a difference between the first pressure and the second pressure. A state of the filter is determined from the difference between the first pressure and the second pressure.

12 Claims, 4 Drawing Sheets

(56) References Cited

U.S. PATENT DOCUMENTS

| | | | |
|---|---|---|---|
| 4,650,462 A | 3/1987 | Desatnick et al. | |
| 4,679,583 A | 7/1987 | Lucas et al. | |
| 4,706,687 A | 11/1987 | Rogers et al. | |
| 4,757,814 A | 7/1988 | Wang et al. | |
| 4,770,654 A | 9/1988 | Rogers et al. | |
| 4,790,816 A | 12/1988 | Sunblom et al. | |
| 4,810,242 A | 3/1989 | Sundblom et al. | |
| 4,840,111 A | 6/1989 | Garnjost | |
| 4,887,636 A | 12/1989 | Rothen | |
| 4,933,843 A | 6/1990 | Scheller et al. | |
| 5,094,260 A | 3/1992 | Stuart et al. | |
| 5,138,838 A | 8/1992 | Crosser | |
| 5,176,628 A | 1/1993 | Charles et al. | |
| 5,239,861 A | 8/1993 | Fujita et al. | |
| 5,279,322 A | 1/1994 | Nakamura et al. | |
| 5,314,295 A | 5/1994 | Lukkari et al. | |
| 5,318,072 A | 6/1994 | Goedecke | |
| 5,417,246 A | 5/1995 | Perkins et al. | |
| 5,549,139 A | 8/1996 | Perkins et al. | |
| 5,571,248 A | 11/1996 | Seetharaman et al. | |
| 5,580,347 A | 12/1996 | Reimels | |
| 5,587,536 A | 12/1996 | Rasmussen | |
| 5,674,194 A | 10/1997 | Jung et al. | |
| 5,829,335 A | 11/1998 | Ewald et al. | |
| 5,846,257 A | 12/1998 | Hood | |
| 5,857,485 A | 1/1999 | Perkins et al. | |
| 5,979,494 A | 11/1999 | Perkins et al. | |
| 6,065,494 A | 5/2000 | Thomsen et al. | |
| 6,155,233 A | 12/2000 | Wade et al. | |
| 6,155,289 A * | 12/2000 | Carlsen et al. | 137/457 |
| 6,450,966 B1 | 9/2002 | Hanna | |
| 6,474,289 B1 * | 11/2002 | Lilly et al. | 123/198 D |
| 6,514,268 B2 | 2/2003 | Finlay et al. | |
| 6,575,990 B1 | 6/2003 | Wang et al. | |
| 6,655,404 B2 | 12/2003 | Hilaire | |
| 6,773,445 B2 | 8/2004 | Finlay et al. | |
| 6,779,541 B2 | 8/2004 | Inayama et al. | |
| 7,089,733 B1 | 8/2006 | Jackson et al. | |
| 7,244,240 B2 | 7/2007 | Nazarifar et al. | |
| 7,335,217 B2 | 2/2008 | Wang et al. | |
| 7,470,277 B2 | 12/2008 | Finlay et al. | |
| 7,814,936 B2 | 10/2010 | Catron | |
| 2002/0069916 A1 | 6/2002 | Ferguson et al. | |
| 2002/0117214 A1 | 8/2002 | Tucker et al. | |
| 2002/0173814 A1 | 11/2002 | Jung et al. | |
| 2002/0174905 A1 | 11/2002 | Latino et al. | |
| 2003/0042182 A1 * | 3/2003 | Moscaritolo | 210/85 |
| 2003/0078609 A1 | 4/2003 | Finlay et al. | |
| 2006/0271082 A1 | 11/2006 | Kirchhevel et al. | |
| 2007/0270735 A1 | 11/2007 | Williams et al. | |
| 2007/0270746 A1 | 11/2007 | King | |
| 2007/0282262 A1 | 12/2007 | Williams et al. | |
| 2008/0082077 A1 | 4/2008 | Williams | |
| 2008/0142093 A1 | 6/2008 | Turner et al. | |
| 2008/0146988 A1 | 6/2008 | Olivera et al. | |
| 2008/0149197 A1 | 6/2008 | Turner et al. | |
| 2008/0168985 A1 | 7/2008 | Turner et al. | |
| 2009/0124962 A1 | 5/2009 | Hopkins et al. | |
| 2009/0203480 A1 | 8/2009 | Petzold et al. | |
| 2009/0259242 A1 | 10/2009 | Gerg et al. | |
| 2009/0270793 A1 | 10/2009 | Domash et al. | |

FOREIGN PATENT DOCUMENTS

| | | |
|---|---|---|
| DE | 198 21 420 C1 | 10/1999 |
| DE | 10247869 A1 | 5/2004 |
| DE | 10341477 | 3/2005 |
| DE | 20 2005 009670 U1 | 9/2005 |
| DE | 10247869 B4 | 2/2007 |
| EP | 0469641 B1 | 6/1989 |
| EP | 0626628 A1 | 11/1994 |
| EP | 0626628 B1 | 12/1997 |
| EP | 0 884 667 A1 | 6/1998 |
| EP | 0673475 B1 | 6/1998 |
| EP | 874163 A2 | 10/1998 |
| EP | 1 172 586 A1 | 1/2002 |
| EP | 1660244 B1 | 12/2006 |
| EP | 1734260 | 12/2006 |
| EP | 2032878 | 12/2009 |
| GB | 792397 | 3/1958 |
| GB | 1 213 723 | 11/1970 |
| GB | 2 016 746 A | 9/1979 |
| GB | 2 389 423 A | 12/2003 |
| JP | 61-18133 | 3/1982 |
| JP | 62-203437 | 12/1987 |
| JP | 5-87779 | 1/1989 |
| JP | 2-223846 | 9/1990 |
| JP | 07259801 A | 10/1995 |
| JP | 09225698 A | 9/1997 |
| JP | 10-339301 | 12/1998 |
| WO | WO 00/78371 A1 | 12/2000 |
| WO | WO 01/64120 A1 | 9/2001 |
| WO | WO 2008/000599 A1 | 1/2008 |
| WO | WO 2008/054944 A1 | 5/2008 |
| WO | WO 2008/105950 A2 | 9/2008 |
| WO | WO 2008/105950 A3 | 9/2008 |
| WO | WO 2008/140537 A1 | 11/2008 |
| WO | WO 2008/147429 | 12/2008 |
| WO | WO 2008/147429 A2 | 12/2008 |
| WO | WO 2008/147429 A3 | 12/2008 |

OTHER PUBLICATIONS

International Searching Authority, PCT International Preliminary Report on Patentability, PCT/US2007/079915, May 15, 2009, 6 pages.

International Searching Authority, PCT International Preliminary Report on Patentability, PCT/US2007/080265, Sep. 1, 2009, 8 pages.

International Searching Authority, PCT International Preliminary Report on Patentability, PCT/US2007/080540, Jun. 23, 2009, 5 pages.

Final Office Action, U.S. Appl. No. 11/610,275, Sep. 14, 2009, 18 pages.

International Searching Authority, PCT International Preliminary Report on Patentability, PCT/US2007/080239, Jun. 16, 2009, 8 pages.

N. Kabei, E. Shimemura; Y. Sakurai, K. Tsuchiya; "A Portable Pneumatic Driving Unit for a Left Ventricular Assist Device"; Int J Artif Organs, 1988, 11(3), 186-90.

Marvin M. Nachlas, M.D. and Melvin P. Siedband, B.A.; "A Simple Portable Pneumatic Pump for External Cardiac Massage"; The American Journal of Cardiology, 1962, 10(1), 107-109.

J.L. Waldeck; "The Development of a Portable Pressure Source for the Static and Dynamic Calibration of Pressure Transducers"; Journal of Wind Engineering and Industrial Aerody, 1987, 26(2), 213-230.

Ellis, George Gollomp, Bernard P.; "Microcomputer-Controlled Precision Pneumatic Pressure Generator"; IEEE Transactions on Instrumentation and Measurement, 1977, 26(3), 214-217.

Whalen, R.L., Briskman, R.N.; "An Electromagnetic Pneumatic Blood Pump Driver"; American Society of Artifical Internal Organs, 1988, 34(3), 721-725.

R. B. Turkentine, I.S. Williams; "Pressure-Operated Shutter for Thin-Film Monitor"; Journal of Physics E: Scientific Instruments, 1979, 12(1).

Richard C. Rogers; "An Inexpensive Picoliter-Volume Pressure Ejection System"; Brain Research Bulletin, 1985, 15(6), 669-671.

Kenneth S. Johnson, Carl L. Beehler, Carole M. Sakamoto-Arnold; "A Submersible Flow Analysis System"; Analytica Chimica Acta, 1986, 179, 245-257.

Alim Abid Tabassum; "Solar Refrigeration: Evaluation of Technical Options and Design of a Solar-Generator-Absorber for a Novel Adsorption Refrigerator".

P. R. Buchanan, S. J. Tavener, S.J. Withy, E. A. Harris; "Recovery of Ventilation Distributions by Gas Wash-out of a Mechanical Pump"; Clinical Physics and Physiological Measurement, 1986, 7(3).

Office Action, U.S. Appl. No. 11/610,275, Nov. 25, 2008, 10 pages.

Office Action, U.S. Appl. No. 11/610,275, Apr. 13, 2009, 16 pages.

(56) References Cited

OTHER PUBLICATIONS

International Search Report for PCT/US2007/080239, Publication No. WO2008/140537, 3 pages.
International Search Report for PCT/US2007/079915, Publication No. WO2008/054944, 2 pages.
International Search Report for PCT/US2007/080265, Publication No. WO2008/105950, 3 pages.
International Search Report for PCT/US2007/080540, Publication No. WO2008/147429, 4 pages.
Document labeled "D1A" titled "oerHi Switzerland" received in an opposition filed Dec. 2, 2011 in the corresponding EP Patent No. EP2099399; Granted Mar. 2, 2011, 4 pages.
Document labeled "D1B" titled "Pneumatik Einheit" received in an opposition filed Dec. 2, 2011 in the corresponding EP Patent No. EP2099399; Granted Mar. 2, 2011, 1 page.
Document labeled "D1C" entitled "OS3 Basic: Pneumatik" received in an opposition filed Dec. 2, 2011 in the corresponding EP Patent No. EP2099399; Granted Mar. 2, 2011, 1 page.
Document labeled "D1D" entitled "SPS Highspeed Vitrektomie Stripper" received in an opposition filed Dec. 2, 2011 in the corresponding EP Patent No. EP2099399; Granted Mar. 2, 2011, 1 page.
Document labeled "D1E" and "D2E" entitled "Oertli Instrumente Ag/Alcon Inc.-Eidesstattliche Erklarung" received in an opposition filed Dec. 2, 2011 in the corresponding EP Patent No. EP2099399; Granted Mar. 2, 2011, 8 pages.
English translation of document labeled "D1E" and "D2E" entitled "Oertli Instrumente AG/Alcon Inc.-Affidavit" received in an opposition filed Dec. 2, 2011 in the corresponding EP Patent No. EP2099399; Granted Mar. 2, 2011, 3 pages.
Document labeled "D1F" entitled "Strukturstuckliste" received in an opposition filed Dec. 2, 2011 in the corresponding EP Patent No. EP2099399; Granted Mar. 2, 2011, 2 pages.
Document labeled "D2A" entitled "Kopie" received in an opposition filed Dec. 2, 2011 in the corresponding EP Patent No. EP2099399; Granted Mar. 2, 2011, 5 pages.
Document labeled "D2B" entitled "Oertli Instrumente AG, PN210062d" received in an opposition filed Dec. 2, 2011 in the corresponding EP Patent No. EP2099399; Granted Mar. 2, 2011, 1 page.
Document labeled "D2C" entitled "OS Basic: Pneumatik; Fast VIT-PN" received in an opposition filed Dec. 2, 2011 in the corresponding EP Patent No. EP2099399; Granted Mar. 2, 2011, 1 page.
Document labeled "D2D" entitled "SPS Highspeed Vitrektomie Stripper" received in an opposition filed Dec. 2, 2011 in the corresponding EP Patent No. EP2099399; Granted Mar. 2, 2011, 1 page.
Document labeled "D2F" entitled "Service Manual, OS3 Basic" received in an opposition filed Dec. 2, 2011 in the corresponding EP Patent No. EP2099399; Granted Mar. 2, 2011, 25 pages.
Document labeled "D2G" entitled "Stuckliste-Pneumatik Einheit" received in an opposition filed Dec. 2, 2011 in the corresponding EP Patent No. EP2099399; Granted Mar. 2, 2011, 2 pages.
Document labeled "D2H" entitled "Stuckliste-Pneumatikeinheit SMC Ventile" received in an opposition filed Dec. 2, 2011 in the corresponding EP Patent No. EP2099399; Granted Mar. 2, 2011, 1 page.
Document labeled "D2I" entitled "Application Note" received in an opposition filed Dec. 2, 2011 in the corresponding EP Patent No. EP2099399; Granted Mar. 2, 2011, 4 pages.
Document labeled "D3" entitled "US Patent No. 5417246" received in an opposition filed in the corresponding EP Patent No. EP2099399; Granted Mar. 2, 2011, 30 pages.
Document labeled "Electronic Receipt" entitled "Empfangsbescheinigung" received in an opposition filed in the corresponding EP Patent No. EP2099399; Granted Mar. 2, 2011, 2 pages.
Document labeled "EP Notice of Opposition—German" entitled "Einspruch gegen ein europaisches Patent" received in an opposition filed Dec. 2, 2011 in the corresponding EP Patent No. EP2099399; Granted Mar. 2, 2011, 5 pages.
English translation of document labeled "Notice of Opposition-German" entitled "Opposition to EP 2099399 of Alcon Inc." received in an opposition filed Dec. 2, 2011 in the corresponding EP Patent No. EP2099399; Granted Mar. 2, 2011, 15 pages.
Document labeled "Notice of Opposition-German" entitled "Isler & Pedrazzini AG" received in an opposition filed Dec. 2, 2011 in the corresponding EP Patent No. EP2099399; Granted Mar. 2, 2011, 18 pages.

\* cited by examiner

GAS PRESSURE MONITOR FOR PNEUMATIC SURGICAL MACHINE

FIELD OF THE INVENTION

The present invention relates to a pneumatic module for a surgical machine and more particularly to a safety filter monitor for such a module.

BACKGROUND OF THE INVENTION

Several conditions of the eye threaten sight. Epiretinal membrane (ERM), also known as macular pucker and cellophane retinopathy, is a condition characterized by growth of a membrane across the macula, or central retina of the eye. This condition may be thought of as the growth of scar tissue across the macula, thus interfering with central vision. The ERM typically contracts, causing distortion of the central retina, thus producing distortion of vision. Most patients will note that either straight objects appear wavy and crooked and/or central vision is reduced, depending on the severity of the condition.

Epiretinal membranes may be associated with other conditions of the eye, however, the large majority are idiopathic, which means that the cause is unknown. Some of the disorders which are occasionally associated with ERM's include previous retinal detachments and surgery thereof, inflammatory conditions (uveitis), retinal tears, and branch retinal vein occlusion (BRVO) and central retinal vein occlusion (CRVO).

Another condition is a macular hole. A macular hole is almost always a spontaneous development that occurs predominantly in aging women. The development of a macular hole progresses through several stages, and with each progressive stage the vision may worsen. It has been postulated that shrinkage of the vitreous humor may produce traction on the fovea (central macula), thereby producing the hole itself. However, the cause of macular holes remains under investigation.

The retina, which lines the inside of the posterior wall of the eye, may occasionally become detached for various reasons. Most commonly, retinal detachment occurs as a result of a tear or hole in the retina, which develops as a result of a posterior vitreous separation (PVS). The retinal tear or hole allows fluid to enter the subretinal space, thus detaching the retina.

The retina receives oxygen and nutrients from the underlying choroid (vascular layer) of the eye. When a retinal detachment occurs, the detached retina begins to dysfunction, and ultimately, necrosis (death) ensues as a result if the retina is not reattached to the underlying choroid. As such, a retinal detachment is an urgent condition. The detached retina should be recognized and treated promptly.

Vitreo-retinal procedures may be appropriate to treat these and other serious conditions of the back of the eye. Vitreo-retinal procedures include a variety of surgical procedures performed to restore, preserve, and enhance vision. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

The vitreous is a normally clear, gel-like substance that fills the center of the eye. It makes up approximately 2/3 of the eye's volume, giving it form and shape before birth. Certain problems affecting the back of the eye may require a vitrectomy, or surgical removal of the vitreous.

A vitrectomy may be performed to clear blood and debris from the eye, to remove scar tissue, or to alleviate traction on the retina. Blood, inflammatory cells, debris, and scar tissue obscure light as it passes through the eye to the retina, resulting in blurred vision. The vitreous is also removed if it is pulling or tugging the retina from its normal position. Some of the most common eye conditions that require vitrectomy include complications from diabetic retinopathy such as retinal detachment or bleeding, macular hole, retinal detachment, pre-retinal membrane fibrosis, bleeding inside the eye (vitreous hemorrhage), injury or infection, and certain problems related to previous eye surgery.

The retinal surgeon performs a vitrectomy with a microscope and special lenses designed to provide a clear image of the back of the eye. Several tiny incisions just a few millimeters in length are made on the sclera. The retinal surgeon inserts microsurgical instruments through the incisions such as a fiber optic light source to illuminate inside the eye, an infusion line to maintain the eye's shape during surgery, and instruments to cut and remove the vitreous.

In a vitrectomy, the surgeon creates three tiny incisions in the eye for three separate instruments. These incisions are placed in the pars plana of the eye, which is located just behind the iris but in front of the retina. The instruments which pass through these incisions include a light pipe, an infusion port, and the vitrectomy cutting device. The light pipe is the equivalent of a microscopic high-intensity flashlight for use within the eye. The infusion port is required to replace fluid in the eye and maintain proper pressure within the eye. The vitrector, or cutting device, works like a tiny guillotine, with an oscillating microscopic cutter to remove the vitreous gel in a slow and controlled fashion. This prevents significant traction on the retina during the removal of the vitreous humor.

The surgical machine used to perform a vitrectomy and other surgeries on the posterior of the eye are very complex. Typically, such an ophthalmic surgical machine includes a main console to which numerous different tools are attached. The main console provides power to and controls the operation of the attached tools.

The attached tools typically include probes, scissors, forceps, illuminators, and infusion lines. Each of these tools is typically attached to the main surgical console. A computer in the main surgical console monitors and controls the operation of these tools. These tools also get their power from the main surgical console. Some of these tools are electrically powered while others are pneumatically powered.

In order to provide pneumatic power to the various tools, the main surgical console has a pneumatic or air distribution module. This pneumatic module conditions and supplies compressed air or gas to power the tools. Typically, the pneumatic module is connected to a cylinder that contains compressed gas. Most commonly, surgeons use cylinders of nitrogen at 3600 psi. The condition and output of these cylinders affect the operation of the surgical machine.

The proper gas pressure must be provided by the pneumatic module to the tools in order to insure their proper operation. Providing too low or too high a gas pressure can lead to safety problems. Too low a gas pressure can lead to underperformance or non-performance of the operation of a tool. Too high a pressure can damage equipment or lead to a malfunction during surgery. In either case, the safety of the patient is compromised.

It would be desirable to incorporate a gas pressure monitor in an ophthalmic surgical machine to protect the patient.

SUMMARY OF THE INVENTION

In one embodiment consistent with the principles of the present invention, the present invention is a gas pressure monitor system for a pneumatically-powered surgical machine. The system includes a first transducer, a second transducer, and a controller. The first transducer is located upstream from a filter and is configured to read a first pressure of a gas before the gas enters the filter. The second transducer is located downstream from the filter and is configured to read a second pressure of a gas after the gas exits the filter. The controller is configured to compute a difference between the first pressure and the second pressure. A state of the filter is determined from the difference between the first pressure and the second pressure.

In another embodiment consistent with the principles of the present invention, the present invention is a gas pressure monitor system for a pneumatically-powered surgical machine. The system includes a first transducer, a second transducer, a coupling, an isolation valve, a pressure release valve, and four manifolds. The first transducer is located upstream from a filter and is configured to read a first pressure of a gas before the gas enters the filter. The second transducer is located downstream from the filter and is configured to read a second pressure of a gas after the gas exits the filter. The coupling is configured to accept gas from a gas source. The isolation valve is located between the first transducer and the filter. The pressure relief valve is located between the coupling and the first transducer. The first manifold fluidly connects the first transducer to the isolation valve. The second manifold fluidly connects the isolation valve to the filter. The third manifold fluidly connects the filter to the second transducer. The fourth manifold fluidly connects the coupling and the pressure relief valve to the first transducer.

In another embodiment consistent with the principles of the present invention, the present invention is a gas pressure monitor system for a pneumatic module. The system includes a first transducer, a second transducer, a coupling, an isolation valve, a pressure release valve, logic, and four manifolds. The first transducer is located upstream from a filter and is configured to read a first pressure of a gas before the gas enters the filter. The second transducer is located downstream from the filter and is configured to read a second pressure of a gas after the gas exits the filter. The coupling is configured to accept gas from a gas source. The isolation valve is located between the first transducer and the filter. The pressure relief valve is located between the coupling and the first transducer. The first manifold fluidly connects the first transducer to the isolation valve. The second manifold fluidly connects the isolation valve to the filter. The third manifold fluidly connects the filter to the second transducer. The fourth manifold fluidly connects the coupling and the pressure relief valve to the first transducer. The logic is configured to compute a difference between the first pressure reading and the second pressure reading. When the difference between the first pressure reading and the second pressure reading is greater than a second amount, an indication that the filter needs service is provided. When the first pressure reading is greater than a first amount, the pressure release valve is opened and the isolation valve is closed. When the second pressure is less than a third amount, the isolation valve is closed.

In another embodiment consistent with the principles of the present invention, the present invention is a method for monitoring gas pressure in a pneumatic module of a surgical machine. The method includes sensing a first pressure of a gas upstream from a filter and sensing a second pressure of a gas downstream from the filter. If the first pressure is greater than a first amount, a pressure relief valve is opened, and an indication of high gas pressure is provided. If the second pressure is less than a second amount, an indication of low gas pressure is provided.

In another embodiment consistent with the principles of the present invention, the present invention is a method for monitoring the state of a filter in a pneumatic module of a surgical machine. The method includes sensing a first pressure of a gas upstream from a filter, sensing a second pressure of a gas downstream from the filter, computing a difference between the first pressure and the second pressure, and comparing the difference to a value to determine a state of the filter.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
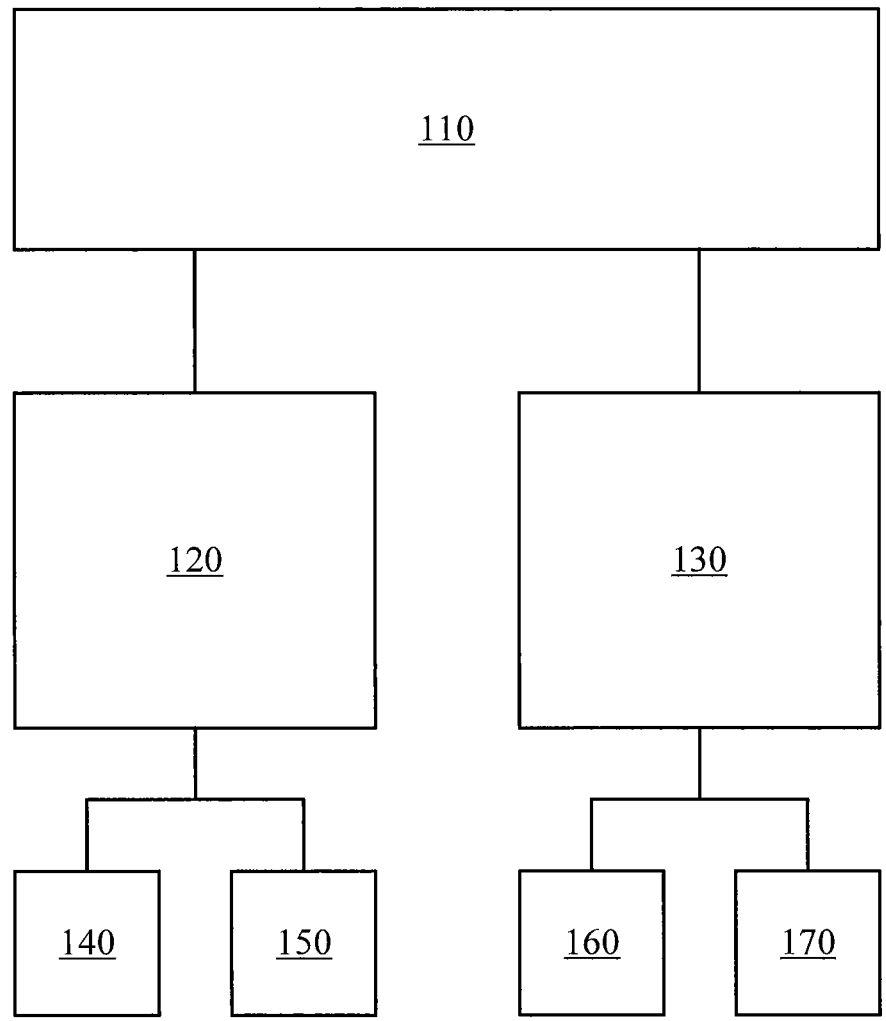
FIG. 1 is a block diagram of a pneumatically-powered ophthalmic surgery machine according to an embodiment of the present invention.

FIG. 1 is a block diagram of a pneumatically powered ophthalmic surgical machine according to an embodiment of the present invention. In FIG. 1, the machine includes gas pressure monitor system 110, proportional controller 120, proportional controller 130, and tools 140, 150, 160, and 170. The tools 140, 150, 160, and 170 can be, for example, scissors, vitrectomy probes, forceps, and injection or extraction modules. Other tools may also be employed with the machine of FIG. 1.

As shown in FIG. 1, gas pressure monitor system 110 is fluidly coupled via a manifold to proportional controller 120 and proportional controller 130. A single manifold may connect gas pressure monitor system 110 to proportional controller 120 and proportional controller 130, or two separate manifolds may connect gas pressure monitor system 110 to proportional controller 120 and proportional controller 130, respectively. Proportional controller 120 is fluidly coupled to tools 140 and 150 by, for example, a manifold and tubing. Likewise proportional controller 130 is fluidly coupled to tools 160 and 170, by, for example, a manifold and tubing.

In operation, the pneumatically powered ophthalmic surgery machine of FIG. 1 operates to assist a surgeon in performing various ophthalmic surgical procedures, such as a vitrectomy. A compressed gas, such as nitrogen, provides the power for tools 140, 150, 160, and 170. The compressed gas passes through gas pressure monitor system 110, through one or more manifolds to proportional controllers 120 and 130, and through additional manifolds and/or tubing to tools 140, 150, 160, and 170.

Gas pressure monitor system 110 functions to monitor the pressure of compressed gas from a gas source as it enters the machine. As further discussed below, gas pressure monitor system acts to ensure the safety of the operation of the machine.

Proportional controllers 120 and 130 serve to distribute the compressed gas received from gas pressure monitor system 110. Proportional controllers 120 and 130 control the pneumatic power delivered to tools 140, 150, 160, and 170.

Tools 140, 150, 160, and 170 are all pneumatically powered. In such a case, compressed gas powers the operation of these tools. Various valves, manifolds, and tubing are used to direct compressed gas from gas pressure monitor system 110, through proportional controllers 120 and 130, and into tools 140, 150,160, and 170. This compressed gas actuates cylinders, for example, in tools 140, 150, 160, and 170.

Figure 2:
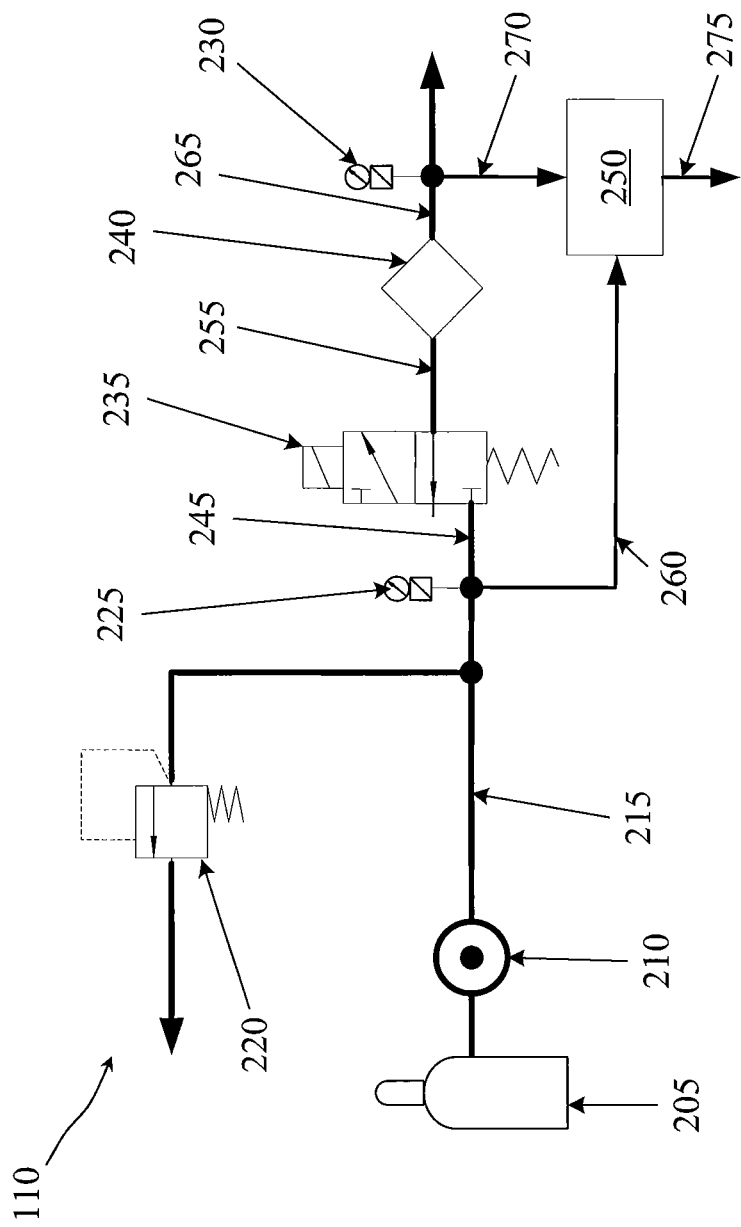
FIG. 2 is a schematic of a gas pressure monitor system for a pneumatically powered surgical machine according to an embodiment of the present invention.

FIG. 2 is a schematic of a gas pressure monitor system for a pneumatically powered surgical machine according to an embodiment of the present invention. In FIG. 2, the gas pressure monitor system includes a gas source 205, coupling 210, manifold 215, pressure release valve 220, first transducer 225, second transducer 230, isolation valve 235, filter 240, manifold 245, controller 250, manifold 255, interface 260, manifold 265, interface 270, and interface 275. While all of these components are depicted in FIG. 2 as being of part of gas pressure monitor system 110, a subset of these components may comprise gas pressure monitor system 110 as described in the appended claims.

In the embodiment of FIG. 2, gas source 205 is fluidly coupled through coupling 210 to manifold 215. Manifold 215 fluidly couples pressure release valve 220, coupling 210, and first transducer 225. In this manner, a single manifold connects gas source 205 to first transducer to 225 and pressure release valve 220.

First transducer 225 is fluidly coupled to isolation valve 235 via manifold 245. Isolation valve 235 is fluidly coupled to filter 240 via manifold 255. Filter 240 is fluidly coupled to second transducer 230 via manifold 265.

Controller 250 receives signals from first transducer 225 via interface 260 and from second transducer 230 via interface 270. In this manner, first transducer 225 is electrically coupled to controller 250 via interface 260. Second transducer 230 is electrically coupled to controller 250 via interface 270. Interface 275 is an output of controller 250. In this example, interface 275 carries output signals from controller 250 to other components of gas pressure monitor system 110 such as isolation valve 235 and pressure release valve 220.

The gas pressure monitor system 110 of FIG. 2 includes gas source 205. Gas source 205 is typically a bottle or cylinder of compressed gas. In many cases, surgeons utilize cylinders of compressed nitrogen. In other cases, surgeons utilize a source of compressed air. In either case, gas source 205 is a source of compressed gas that provides the pneumatic power for the pneumatically powered ophthalmic surgery machine.

Coupling 210 is an input port that receives compressed gas from gas source 205. In most cases, coupling 210 is a standard connector on a manifold designed to connect to tubing from gas source 205. Coupling 210 allows compressed gas from gas source 205 to enter gas pressure monitor system 110 and provide pneumatic power to the machine.

Pressure release valve 220 is a valve configured to open if the pressure in manifold 215 is too high. In this manner, pressure release valve 220 operates to release compressed gas from manifold 215 if the pressure of that compressed gas exceeds a certain threshold. In many cases, pressure release valve 220 has a set point that can be adjusted. For example, pressure release valve 220 may have a user adjustable set point. In such a case, an engineer may be able to set the set point at 200 lbs per square inch (psi), and pressure release valve 220 opens when the pressure of the compressed gas in manifold 215 exceeds 200 psi. In other embodiments consistent with the present invention, pressure release valve 220 is controlled by controller 250. In such a case, controller 250 maybe able to send electrical signals via interface 275 to controller pressure release valve 220.

In the embodiment of FIG. 2, isolation valve 235 is a standard two way valve. In this case, isolation valve 235 has two positions—on and off. When isolation valve 235 is turned on, gas is allowed to flow from manifold 245 to manifold 255. When isolation valve 235 is turned off, gas is not allowed to flow from manifold 245 to manifold 255. In the embodiment of FIG. 2, isolation valve 235 is depicted as being turned off. Isolation valve 235 maybe controlled by controller 250. In this manner, controller 250 sends signals via interface 275 to isolation valve 235 to control its operation. For example, controller 250 may send a signal via interface 275 to isolation valve 235 to turn it to an on position.

In the embodiment of FIG. 2, filter 240 serves to filter compressed gas passing from manifold 255 to manifold 265. Filter 240 also acts as a water separator. In this manner, filter 240 serves to filter objects from the compressed gas as it passes from manifold 255 to manifold 265. Filter 240 also serves to remove water from the compressed gas as it passes from manifold 255 to manifold 265. In the embodiment of FIG. 2, filter 240 filters the compressed gas before it enters the remainder of the machine.

First transducer 225 and second transducer 230 operate to read an atmospheric pressure of the gas contained in manifold 215 and manifold 265 respectfully. In this manner, first transducer 225 reads the pressure of the compressed gas after it exits gas source 205, enters coupling 210, and enters manifold 215. Likewise, second transducer 230 reads the pressure of the compressed gas as it exits filter 240 and enters manifold 265. In other words, first transducer 225 reads the pressure of the compressed gas that is located in the manifold adjacent to first transducer 225. Likewise, second transducer 230 reads the pressure of the compressed gas that is adjacent to it in manifold 265.

In the embodiment of FIG. 2, first transducer 225 and second transducer 230 are common pressure transducers. First transducer 225 and second transducer 230 are capable of reading pressure of a compressed gas and sending an electrical signal containing information about the pressure of the compressed gas to controller 250. First transducer 225 sends a signal corresponding to the pressure of the compressed gas that it reads via interface 260. Likewise, second transducer 230 sends a signal about the pressure of the compressed gas via interface 270 to controller 250.

Controller 250 is typically an intergraded circuit capable of performing logic functions. Controller 250 is typically in the form of a standard intergraded circuit package with power, input, and output pins. In various embodiments, controller 250 is a valve controller or a targeted device controller. In such a case, controller 250 performs specific control functions targeted to a specific device, such as a valve. For an example, a valve controller has the basic functionality to control a valve. In other embodiments, controller 250 is a microprocessor. In such a case, controller 250 is programmable so that it can function to control valves in gas pressure monitor system 110 as well as other components of the machine. In other cases, controller 250 is not a programmable microprocessor, but instead is a special purpose controller configured to control different valves that perform different functions.

Controller 250 is configured to receive signals from first transducer 225 via interface 260 and from second transducer 230 via interface 270. These signals, for example, correspond to readings of gas pressure in manifold 215 and manifold 265, respectively. Controller 250 is also configured to send output signals via interface 275. As noted, these output signals from controller 250 are typically sent to valves, such as isolation valve 235, via interface 275.

Manifolds 215, 245, 255, 265 are all configured to carry compressed gas. In the embodiment of FIG. 2, these manifolds are machined out of a metal, such as aluminum. These manifolds are air tight, contain various fittings and couplings, and are designed to withstand relatively high gas pressures. These manifolds maybe manufactured as individual pieces or they maybe manufactured as a single piece. For example, manifold 215 and manifold 245 maybe a single continuous manifold. In this manner, manifold 215 and manifold 245 are machined from a single piece of aluminum. In such a case, one end of manifold 215 and manifold 245 is designed to house coupling 210, another end is designed to house pressure release valve 220, another end is designed to accommodate isolation valve 235, and another end is designed to accommodate first transducer 225.

Interface 260 and interface 270 are designed to carry signals from first transducer 225 and second transducer 230 to controller 250. In this case, interface 260 and interface 270 are common electrical conductors such as wires. Likewise, interface 275 carries signals from controller 250 to isolation valve 235, for example. Interface 275 maybe one or more wires or buses designed to carry electrical or data signals.

The gas pressure monitor system 110 of FIG. 2 provides compressed gas to the remainder of a surgical machine. In operation, compressed gas from gas source 205 passes through coupling 210 and into manifolds 215 and 245. First transducer 225 reads the pressure of the compressed gas in manifolds 215 and 245. Compressed gas is also allowed to travel from manifolds 215 to the input of pressure release valve 220. As depicted in FIG. 2, pressure release valve 220 is turned off. Therefore, the pressure of compressed gas is allowed to maintain itself in manifolds 215 and 245. Isolation valve 235 is also turned off.

First transducer 225 reads the pressure of the compressed gas in manifold 215 and 245. If the pressure of the compressed gas is too great, pressure release valve 220 opens and allows the compressed gas to vent to the atmosphere. If the pressure of the compressed gas in manifolds 215 and 245 is too low, then isolation valve 235 remains in the closed or off position. In this manner, first transducer 225 reads a pressure of the compressed gas after it enters gas pressure monitor system 110. If the pressure is too high, pressure release valve 220 is opened. If the pressure is too low, isolation valve 235 remains closed to prevent the low pressure gas from entering the remainder of the system. If the pressure of the compressed gas is within an acceptable range, then isolation valve 235 is opened and the compressed gas is allowed to pass into manifold 255, through filter 240, and into manifold 265.

When the compressed gas enters manifold 265, second transducer 230 measures the pressure of that gas. First transducer 225 measures the pressure of the compressed gas in manifolds 215 and 245 and sends a signal corresponding to this pressure via interface 260 to controller 250. Likewise, second transducer 230 measures the pressure of the compressed gas in manifold 265 (after it has passed through filter 240) and sends a signal corresponding to this pressure via interface 270 to controller 250. Controller 250 compares the pressure read by first transducer 225 to the pressure read by second transducer 230. For example, controller 250 may calculate a difference between the pressure read by second transducer 230 and the pressure read by first transducer 225. This difference corresponds to a pressure drop across filter 240.

In some cases, as filter 240 wears, it becomes less efficient at transferring compressed gas. In such a case, the pressure read by the first transducer 225 is higher than the pressure read by second transducer 230. This means that a pressure drop has occurred across filter 240. As filter 240 becomes more worn or more dirty, the pressure of the compressed gas in manifold 265 as read by second transducer 230 may drop to a level that is too low to safely operate the machine. In such a case, filter 240 needs to be replaced or serviced. In this manner, first transducer 225 and second transducer 230 serve to monitor a state of filter 240. If the state of filter 240 is such that it needs to be serviced or replaced, then controller 250 may provide an indication in the form of illuminating a light emitting diode on a surgical console to indicate that filter 240 needs to be replaced or serviced. In addition, if the pressure read by second transducer 230 falls below a safe level, then controller 250 may turn isolation valve 235 off.

The gas pressure monitor system 110 of FIG. 2 implements various safety features in the ophthalmic surgery machine of FIG. 1. The first of these features is to cause high pressure compressed gas to be vented via pressure release valve 220 so that it does not damage the rest of the surgical machine. In addition, venting high pressure compressed gas via pressure release valve 220 helps to prevent injury to the patient. In this case, if compressed gas with too high of pressure were allowed to enter the remainder of the surgical machine, the tools 140, 150, 160, and 170 may malfunction and injure a patient. In addition, the high pressure compressed gas may damage various components of the surgical machine. Therefore, if controller 250 receives a signal indicating that the pressure of the compressed gas in manifolds 215 and 245 is above a safe level, then controller 250 opens pressure release valve 220. Alternatively, pressure release valve 220 may be set at a set point equal to the upper limit of a safe range of pressure for compressed gas. In such a case, if the pressure of the compressed gas in manifold 215 exceeds the set point, pressure release valve 220 opens.

The gas pressure monitor system 110 of FIG. 2 also prevents the introduction of compressed gas with too low a pressure into the remainder of the surgical machine. In this case, first transducer 225 senses that the compressed gas in manifold or manifold 245 is at too low a pressure. First transducer 225 sends a signal via interface 260 to controller 250 indicating such. Controller 250 receives this signal and causes isolation valve 235 to remain closed. In this manner, compressed gas in manifold 245 is not allowed to pass into manifold 255 and the remainder of the machine. If the pressure of the compressed gas is too low, then the surgical machine may not operate properly. For example, if the pressure of the compressed gas is too low, then the pneumatic power provided to tools 140, 150, 160, and 170 may not be sufficient to safely operate them. In such a case, the unsafe operation of these tools may injure the patient.

The gas pressure monitor system 110 of FIG. 2 also allow for the constant monitoring of the state of filter 240. In this case, first transducer 225 and second transducer 230 act in tandem to monitor the condition of filter 240. If filter 240 were to become clogged, for example, then the surgical machine may not be operated safely. In such a case, controller 250 receives signals from first transducer 225 and second transducer 230 indicating this unsafe condition. In addition, first transducer 225 and second transducer 230 can constantly monitor the condition of filter 240 to ensure that it is operating properly. In such a case, controller 250 may provide an indication that filter 240 may need to be repaired or replaced. Typically, a pressure reading by second transducer 230 of the compressed gas in manifold 265 (after it has passed through filter 240) provides an indication of the state of the filter 240. In one case, second transducer 230 may determine that the pressure of the compressed gas in manifold 265 is below a safe level. In such a case, controller 250 may close or turn off the isolation valve 235. This prevents the low pressure compressed gas from entering the remainder of the machine and causing unsafe operation.

Figure 3:
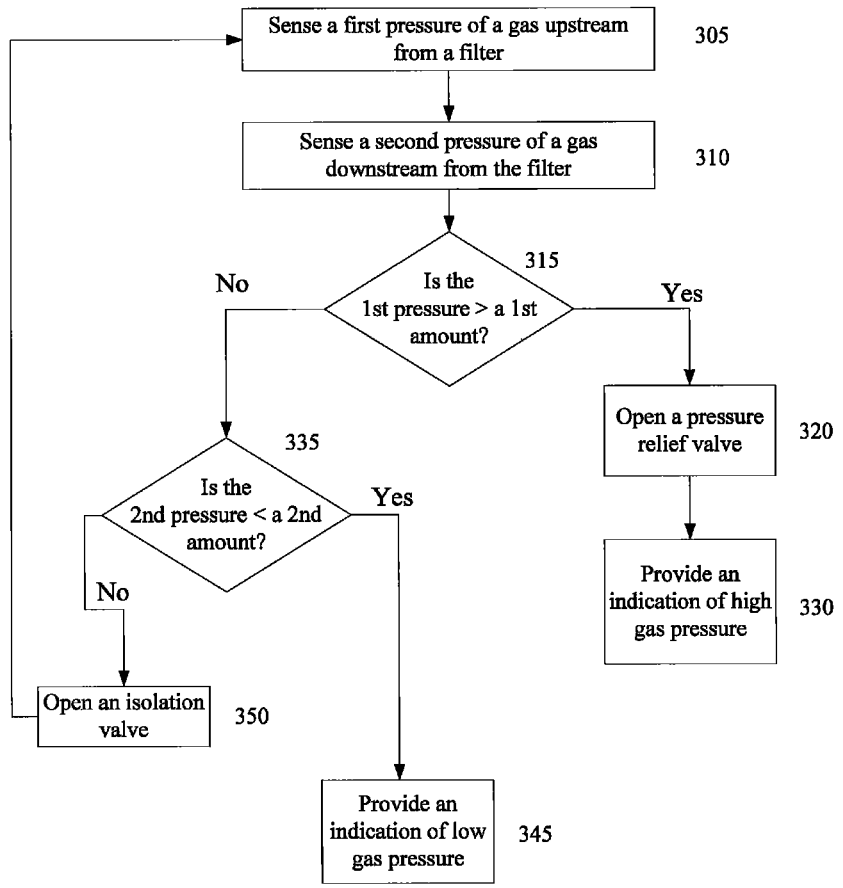
FIG. 3 is a flow chart of one method of operation according to an embodiment of the present invention.

FIG. 3 is a flow chart of one method of operation according to an embodiment of the present invention. In FIG. 3, a first pressure of a gas upstream from a filter is sensed in 305. In 310, a second pressure of a gas downstream from the filter is sensed. In 315 a determination is made as to whether the first pressure is greater than a first amount. In 315, if the first pressure is greater than a first amount, then in 320, a pressure relief valve is opened. In 330 an indication of high gas pressure is provided. If the first pressure is not greater than a first amount in 315, then in 335 a determination is made as to whether the second pressure is less than the second amount. An indication of low gas pressure is provided in 345. If the second pressure is not less than a second amount in 335, then an isolation valve is opened in 350. After the isolation valve is opened in 350, the process returns to 305 and a first pressure of a gas upstream from a filter is sensed.

In the embodiment of FIG. 3, the gas pressure monitor system 110 senses a first gas pressure on one side of a filter and a second gas pressure on the other side of the filter. If the first gas pressure upstream from the filter is greater than a safe amount, then the pressure release valve is open to vent the high pressure gas. If the second pressure reading, corresponding to the gas pressure downstream from the filter is less than a safe amount, then the isolation valve remains in the closed position thus preventing the low pressure gas from reaching the remainder of the system and possibly causing an unsafe condition. In the embodiment of FIG. 3, gas pressure monitor system serves to ensure that the pressure of the compressed gas entering of the ophthalmic surgical machine is within a safe range.

Figure 4:
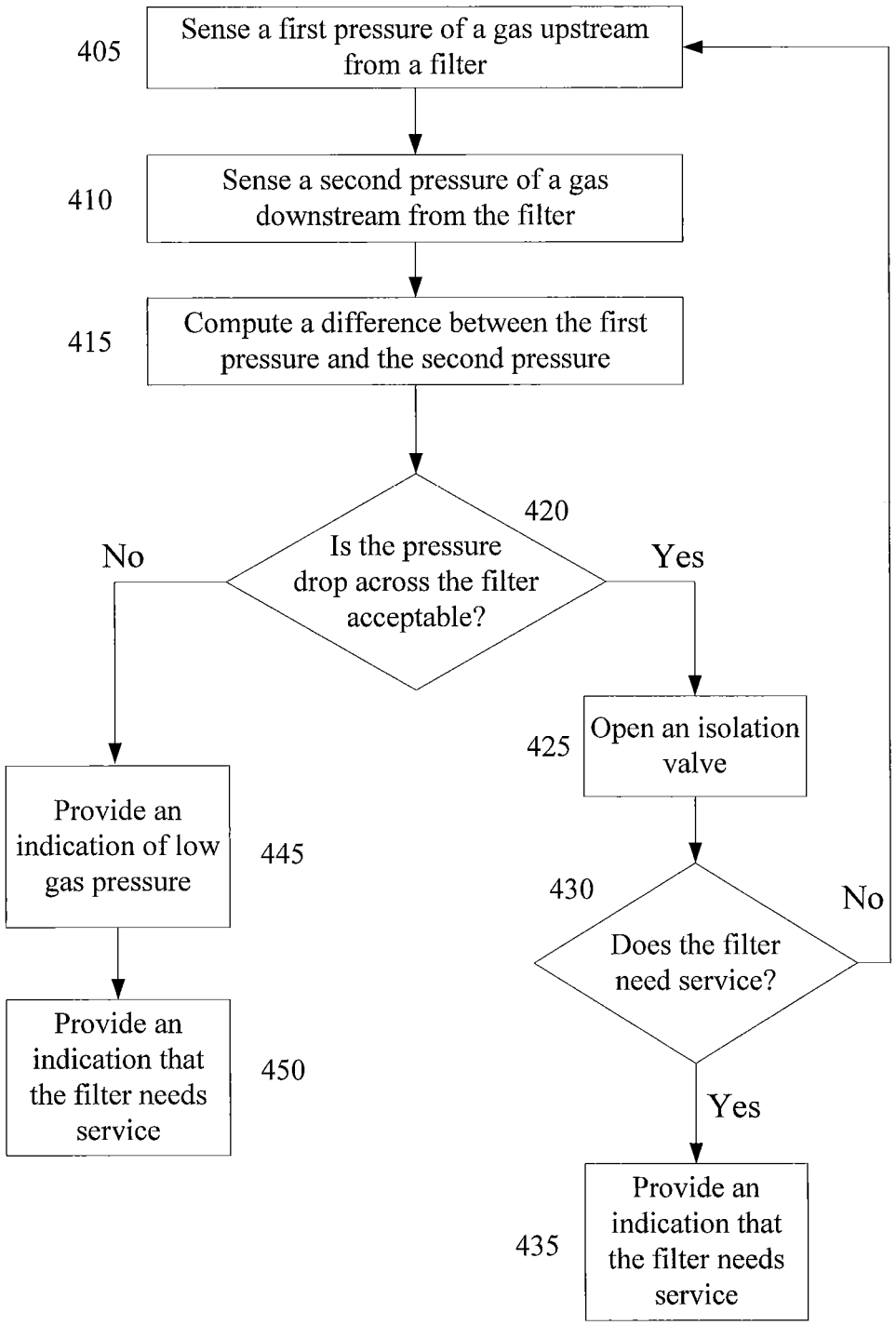
FIG. 4 is a flow chart of one method of operation according to an embodiment of the present invention.

FIG. 4 is a flow chart of another method of operation according to an embodiment of the present invention. In 405, a first pressure of a gas upstream from a filter is sensed. In 410, a second pressure of a gas downstream from the filter is sensed. In 415, the difference between the first pressure and the second pressure is computed. In 420, a determination is made as to the pressure drop across the filter. In 420, if the pressure drop across the filter is acceptable, then in 425 an isolation valve is opened. In 430, a determination is made as to whether the filter needs service. For example, this determination can be based on the difference between the first pressure and the second pressure computed in 415. If the filter needs service in 430, then in 435 an indication that the filter needs service is provided. In 430, if the filter does not need service, then the process returns to 405, and a first pressure of a gas upstream from a filter is sensed.

In 420, if the pressure drop across the filter is not acceptable, then in 445, an indication of low gas pressure is provided. In 450, and indication that the filter needs service is provided.

In the embodiment of FIG. 4, the first pressure reading and the second pressure reading are used to determine a state of the filter. In addition, these pressure readings also determine an unsafe condition for the surgical machine. The difference between the first pressure (upstream from the filter) and the second pressure (downstream from the filter) corresponds to a pressure drop across the filter. If the pressure drop across the filter is too great, this indicates that the filter needs to be replaced or serviced. In one case, if the filter is clogged, then the pressure drop across the filter can be very great leading to an unsafe operation of the machine. The gas pressure monitor system 110 of the present invention thus ensure the safe operation of the machine and also ensures that a patient will not be harmed by the operation of the machine with an unsafe gas pressure.

From the above, it may be appreciated that the present invention provides an improved system and methods for monitoring the gas pressure in a pneumatic module of a surgical machine. The present invention provides safety features designed to protect the patient and the surgical machine from harm due to high or low gas pressure. In addition, the present invention provides a system for monitoring a filter component of the pneumatic module. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A gas pressure monitor system for a pneumatically-powered surgical machine comprising:
    a first transducer located upstream from a filter, the first transducer adapted to read a first pressure of a gas before the gas enters the filter;
    a second transducer located downstream from the filter, the second transducer adapted to read a second pressure of a gas after the gas exits the filter;
    a controller adapted to compute a difference between the first pressure and the second pressure; and
    an isolation valve coupled to a fluid pathway that includes the first transducer, second transducer, and filter;
    wherein the controller is adapted to determine a state of the filter from the difference between the first pressure and the second pressure;
    wherein the controller is adapted to close the isolation valve unless:
    a) the first pressure is within a selected range of pressures; and
    b) the second pressure is greater than a selected pressure.

2. The system of claim 1 wherein the controller is adapted to indicate a need for a filter service when the difference between the first pressure and the second pressure is greater than the predetermined amount.

3. The system of claim 1 wherein the isolation valve is fluidly coupled to the first transducer via a manifold.

4. The system of claim 2 wherein the controller is adapted to indicate a need for a filter service by illuminating a light emitting diode.

5. The system of claim 1 wherein the controller is further adapted to determine a useful life of the filter using the difference between the first pressure and the second pressure.

6. The system of claim 1, further comprising a pressure relief valve upstream of the filter.

7. The system of claim 6, wherein the controller is configured to open the pressure relief valve if the first pressure is greater than a first amount.

8. The system of claim 6, wherein the pressure relief valve is selectable between one of an open condition and a closed condition, the relief valve in the open condition when the first pressure meets or exceeds a selected pressure and the relief valve in the closed position when the first pressure is less than the selected pressure.

9. A gas pressure monitor system for a pneumatically-powered surgical machine comprising:
   a filter;
   a first transducer located upstream from the filter, the first transducer configured to read a first pressure of a gas before the gas enters the filter;
   a second transducer located downstream from the filter, the second transducer configured to read a second pressure of a gas after the gas exits the filter;
   an isolation valve coupled to a fluid pathway that includes the first transducer, second transducer, and filter; and
   a controller adapted to receive the first pressure from the first transducer and the second pressure from the second transducer and compute a pressure difference between the first pressure and the second pressure, the controller further adapted to close the isolation valve when the pressure difference is above a selected pressure difference.

10. The gas pressure monitor system of claim 9, wherein the controller is further adapted to indicate a state of the filter from the difference between the first pressure and the second pressure.

11. The system of claim 9, further comprising a pressure relief valve upstream of the filter.

12. The system of claim 11, wherein the controller is adapted to open the pressure relief valve if the first pressure is greater than a selected pressure.

* * * * *